United States Patent [19]

Costanzi et al.

[11] Patent Number: 5,216,103
[45] Date of Patent: Jun. 1, 1993

[54] SILICONIC U.V. STABILIZERS CONTAINING REACTIVE GROUPS

[75] Inventors: Silvestro Costanzi; Carlo Neri; Rossella Farris, all of Milan, Italy

[73] Assignee: Enichem Synthesis S.p.A., Palermo, Italy

[21] Appl. No.: 774,328

[22] Filed: Oct. 10, 1991

[30] Foreign Application Priority Data

Oct. 12, 1990 [IT] Italy .................. 21718 A/90

[51] Int. Cl.$^5$ ............................................ C08G 77/06
[52] U.S. Cl. .................................... 528/14; 528/18; 528/19; 528/27; 528/28; 528/38; 544/69; 546/14
[58] Field of Search ............ 546/14; 544/69; 528/28, 528/38, 27, 18, 19, 14

[56] References Cited

U.S. PATENT DOCUMENTS 5,051,458 9/1991 Constanzi et al. .................. 528/18

Primary Examiner—Melvyn I. Marquis
Attorney, Agent, or Firm—Oblon, Spivak, McClelland, Maier & Neustadt

[57] ABSTRACT

Polymeric stabilizers having a polysiloxanic structure contain reactive groups which can be linked to the polymeric structure to be stabilized and sterically hindered piperidinic groups. These polymeric stabilizers are particularly suitable for the stabilization of organic polymers against U.V. radiation and heat, when it is required for them not to be extracted by solvents, fats or soaps.

10 Claims, No Drawings

SILICONIC U.V. STABILIZERS CONTAINING REACTIVE GROUPS

The present invention concerns compounds which are used as stabilizers for organic polymers against ultra-violet radiation, and heat, containing sterically hindered piperidinic groups in the molecule, and reactive groups which can be linked to the polymeric structure to be stabilized.

The present invention also concerns procedures for the preparation of these stabilizing compounds and the stabilized polymeric compositions.

It is known that organic polymers undergo degradation with time, due to exposure to atmospheric agents, and above all to ultra-violet radiation; they are also easily degradable during work and transformation processes because of the high temperatures reached.

This degradation causes a lowering of the physical characteristics of the organic polymers, for example a decrease in the breaking load and flexibility, as well as changes in the optical properties of the product. To fight this degradation, stabilizing compounds are normally introduced into the organic polymer.

A group of compounds widely used for this purpose is that of sterically hindered amines.

U.S. Pat. Nos. 4325864 and 4346188 describe, for example, the use of derivatives of pyrrolidine as UV stabilizers and U.S. Pat. No. 3840494 explains the use of esters of 2,2,6,6-tetraalkylpiperidine-4-olo.

In patent applications EP 162524 and IT 21935 A/86, derivatives of pyrrolidine, morpholine and piperidine which also have a hydrolyzing sililate function in the molecule, are also described.

These compounds create, by hydrolysis of the sililate function, complex resinous structures which can last for a long time inside the organic polymer in which they are incorporated.

The creation of these complex resinous structures inside the organic polymer to be stabilized is not easily controllable, however, which means that different products are obtained each time.

A group of polymeric stabilizing compounds, including sterically hindered piperidinic groups, which are easily obtained in well-defined, pre-established structures and which can therefore be incorporated in a homogeneous and easily controllable way into the polymer to be stabilized, is described in Italian patent application No. 20762 A/88 filed by the same Applicant.

However, even if the incorporation of the piperidinic stabilizer in a polymeric structure allows its homogeneous mixture within the polymeric materials to be stabilized, and has a long-lasting effect inside the organic polymer, there are certain cases where these stabilizers do not give a sufficient guarantee for the uses for which they are destined. For example, when the manufactures come into contact with particular solvents which are capable of extracting the stabilizing siloxanic polymer or are destined to be put in contact with food in which case there must be the absolute guarantee that the additive does not move in any way towards the surface of the manufacture.

The present invention consequently concerns a new group of polymeric stabilizers which overcomes all the above-mentioned inconveniences involved in the known art In particular, a new group of polymeric stabilizing compounds has been found, according to the present invention, which includes, apart from the sterically hindered piperidinic groups, reactive organic group which can be linked to the polymeric structure to be stabilized.

In accordance with this, one aspect of the present invention concerns stabilizing polymeric compounds which are defined with the following formula: (I)

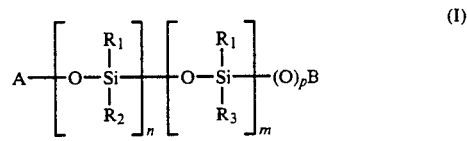

where, m and n, either the same or different, are two integers between 1 and 50, A and B either the same or different can be H, —Si(CH$_3$)$_3$, a linear or branched chain C$_1$-C$_6$ alkyl radical or A and B may jointly stand for a direct bond allowing for a cyclic structure, p is O when A and B are a direct bond and is 1 when A and B are not a direct bond R$_1$ is a methyl, phenyl, alkoxyl radical —OH,— —OSi(OR)$_3$, with R as a linear or branched alkyl radical, —OSi(CH$_3$)$_3$

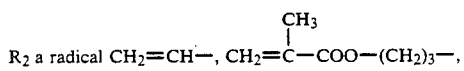

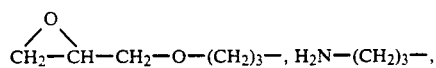

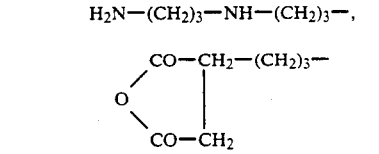

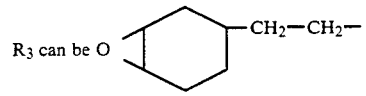

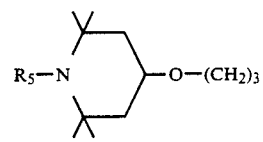

(2,2,6,6-tetramethylpiperidinyl-4-oxypropyl)

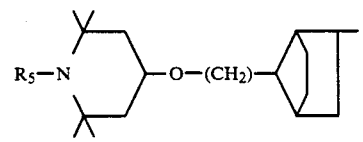

(2,2,6,6-tetramethylpiperidinyl-4-oxymethylen-norbornyl)

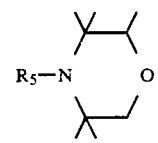

(3,3,5,5 tetramethyl-2-methylene morpholine).

where $R_5$ can be $-H$, $-CH_3$, $C_6H_5-CH_2-$.

The stabilizers of the present invention, corresponding to the above formula (I), are polymers having a random distribution of monomeric unities, and a linear and/or cyclic structure.

In particular, they have a linear structure when A and B, either the same or different, represent a hydrogen atom, a $-Si(CH_3)_3$ group or an alkyl radical whereas they have a cyclic structure when A and B jointly represent a direct bond.

In the case of a linear structure, stabilizers are preferred where the total number of monomeric units (n+m) ranges from 4 to 50, whereas in the case of a cyclic structure it is preferable to have stabilizers where (m+n) is a number between 3 and 7.

In particular, in case of stabilizers with linear structure, it is preferable to have stabilizers where $R_1$ is $CH_3$ whereas $R_3$ is a group corresponding to the formula

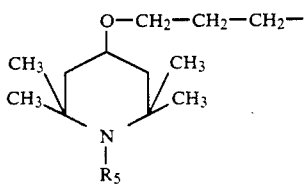

where $R_5$ has the above-mentioned meaning.

When the radical R, having general formula (I), is a $-OSi(OR)_3$ or $-OSi(CH_3)_3$ group, these groups, in the presence of small quantities of water, can cause bridge structures linking two molecules of (I), with the release of 2 ROH moles. These structures are also subject of the present invention.

The polymeric stabilizing compounds of the present invention, corresponding to the general formula (I) in which A and B represent a hydrogen atom, can be easily prepared by mixing, in the required ratios and depending on the value of n and m respectively to be reached, dialkoxysilanes corresponding to the general formula (II)

where $R_1$ and $R_2$ have the above meaning whereas $R_6$ is an alkyl group with from 1 to 4 carbon atoms, with dialkoxysilanes corresponding to the general formula (III)

where $R_1$, $R_3$ and $R_6$ have the above meaning, and making them react in the presence of water and a suitable catalyst. The reaction is the following:

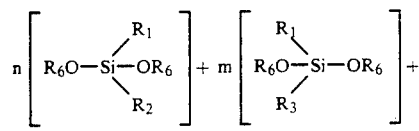

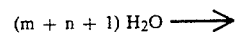

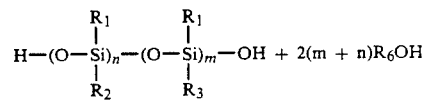

The reaction is carried out at the reflux temperature of the reagents for the time necessary to assure that the presence of the reagents is no longer detected by gas chromatography analysis.

The reaction time generally ranges from 2 to 10 hours.

Reaction catalysts used are tin dibutyllaurate, zinc octoate, tin octoate and alkaline hydroxides. The concentration of the catalyst can range from 0.005 to 0.5% by weight with respect to the products used for the reaction.

At the end of the reaction an organic solvent generally chosen from saturated or unsaturated hydrocarbons, is added which, by dissolving the polymer, causes separation of the water.

The extraction solvent is chosen from aliphatic, cycloaliphatic and aromatic hydrocarbons such as heptane, cyclohexane, toluene.

After eliminating the solvent by distillation, the required polymeric product is obtained, together with a certain amount of cyclic product. Two products are in fact obtained

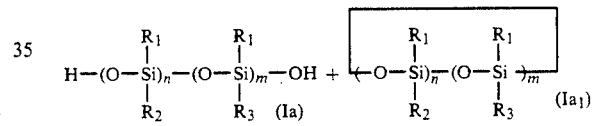

where $R_1$, $R_2$, $R_3$, m and n have the above-defined meaning. The quantities by weight of the two structures in the final mixture depend on the reaction conditions.

Generally, operating at 140° C. for 6-8 hours products containing 80-85% of Ia are obtained.

The dialkoxysilanic products corresponding to the formula of structure II

where $R_1$, $R_2$, $R_6$ have the above-mentioned meaning, are commercial products, whereas the dialkoxysilanic products corresponding to the formula of structure $R_4--Si(R_1R_3)-O-R_4$ (III)
where $R_1$ and $R_3$ and $R_4$ have the above defined meaning, and Ry is an alkyl radical can be synthesized in accordance with patent application 21935 A/86 filed by the same Applicant.

The polymeric stabilizing compounds corresponding to the formula of structure (I) in which at least either A or B is a $-Si(CH_3)_3$ group can be synthesized by reacting the corresponding polymeric products having the formula of structure Ia with one of the following compounds $(CH_3)_3$ Si Cl (trimethylchlorosilane)

$(CH_3)_3-Si-O-Si-(CH_3)_3$ hexamethyldisiloxane (CH$_3$)$_3$—Si—NH—Si(CH$_3$)$_3$ hexamethyldisilazane
The reactions are the following

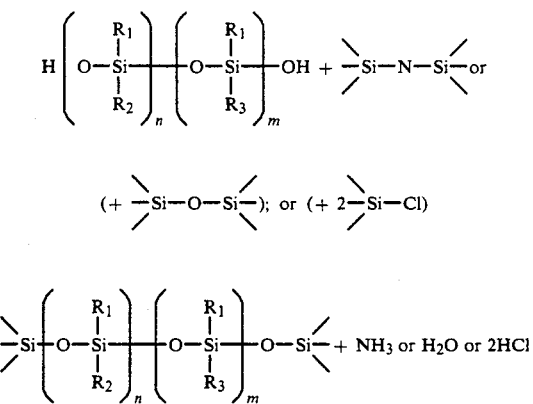

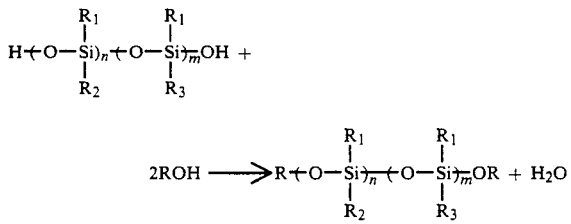

The reaction is carried out at a temperature ranging from 20 to 120° C. preferably between 40 and 80° C. for a period of 1 to 5 hours. The above reactions can be carried out in the presence of small quantities of KOH (0.05% by weight with respect to the siliconic polymer) which is eliminated at the end of the reaction by washing the product with water. The polymeric compounds of the present invention corresponding to the general formula I in which A and B represent a linear or branched alkylic-R$_5$ radical containing from 1 to 6 carbon atoms, can be synthesized starting from $$H(\!-\!O\!-\!\underset{\underset{R_2}{|}}{\overset{\overset{R_1}{|}}{Si}})_n\!-\!(\!O\!-\!\underset{\underset{R_3}{|}}{\overset{\overset{R_1}{|}}{Si}})_m\!OH \;+$$

$$2ROH \longrightarrow R(\!-\!O\!-\!\underset{\underset{R_2}{|}}{\overset{\overset{R_1}{|}}{Si}})_n\!-\!(\!O\!-\!\underset{\underset{R_3}{|}}{\overset{\overset{R_1}{|}}{Si}})_m\!OR \;+\; H_2O$$

The above reaction is carried out in the presence of Catalysts in quantities of approx. 0.5% by weight with respect to the polymer and at temperatures normally ranging from 80 to 130° C. over a period ranging from 1 to 8 hours.

Catalysts suitable for the purpose are the above-mentioned KOH, Zn oxide, tin dibutyldilaurate, tin butyltrilaurate, tin tributyllaurate, alkaline metal alcoholates (CH$_3$ONa, C$_2$H$_5$ONa etc).

Finally, the polymeric products corresponding to the formula of structure (I) in which at least 90% of the molecules have a cyclic structure of the type Ib shown above, can be synthesized starting from the previous linear products at a reaction temperature ranging from 130 to 180° C. and under vacuum of 0.5-2 mm Hg.

The reaction is normally carried out in the presence of small quantities of KOH (0.05%–0.1% by weight of the weight of the siliconic product) for a period of between 2 and 5 hours.

Alternatively, the same product can be obtained by hydrolysis of the two corresponding dialkoxysilane or dichlorosilane monomers in the required ratios.

The molar ratios of the two components of the final polymer range in this case from 1 mole of monomer containing the reactive group for every 3 moles of monomer containing the sterically hindered amine up to 1 mole for each mole.

The polymeric products of the following invention are characterized by the fact that they have a reactive function which links them to the polymer matrix or reinforcing material of the plastic polymer or charges, thus preventing the stabilizer from leaving the matrix or improving the adhesion between matrix and support.

As already specified, these characteristics are particularly important not only for delaying the degradation of the polymers exposed to UV radiation, but also for assuring that the stabilizer is not extracted by solvents, fats or soaps.

This is particularly necessary when the organic manufactures are destined to come into contact with food or for the production of composite manufactures composed of multilayers of organic polymers or polymer and inorganic support.

In the latter cases, the movement of the additive almost always causes detachment of the various layers, loss of the mechanical characteristics of the manufacture and a more rapid degradation of the organic material.

The siliconic products described below can be used as specified.

In one form of application, the siliconic products containing double reactive bonds can be added to the organic polymer to be stabilized in the compounding phase together with small quantities of organic peroxide, which by stimulating the production of radicals allows the additive to become linked to the polymeric matrix during the work process at high temperatures.

This technology is applied in the production of manufactures in cross-linked LDPE during the extrusion phase.

More generically, the products claimed are added as additives either in the final phase of the synthesis process or in the production phase of the manufactures; for example they can be added in the final phase of the synthesis process of rubbers (butadiene styrene, butadiene acrylonitrile) or ABS resins (acrylonitrile butadiene styrene), EPDM (ethylene propylene norbornadiene), in which the additive is linked by thermal grafting.

The addition of products in the preparation phase of manufactures is however the most widely used in the art in that it allows the addition level to be in conformance with the required characteristics of the manufacture. Polymers suitable for the purpose can be polyolefins (LDPE, LLDPE HDPE,PP), copolymers of these with acrylic acid or maleic anhydride, EPDM, synthetic rubber, terpolymers (ABS), polyesters, polyamides, polycarbonates, polyurethanes, water-soluble polyamides normally used in sheet plating and for the protective covering of works of art.

The siliconic compounds can be added either alone or combined with other additives normally used in the art, which are based on sterically hindered phenol such as those sold under the name of Anox 20, Anox PP18 and BHT, phosphites and/or phosphonites such as those sold under the name of Ultranox 626, Weston 618, Alkanox 240, Sandostab PEPQ, organic compounds containing sulfur of the DSTDP, DLTDP type.

These compounds can also be combined with other UV light stabilizers such as hydroxybenzotriazoles, hydroxybenzophenones, organic compounds of Ni, hydroxybenzoates or other similar products.

The quantity of siliconic additive normally used ranges from 0.05% to 1% by weight of the resin to be stabilized, preferred quantities ranging from 0.1% to 0.8% by weight of the resin.

Some examples, which do not limit the present invention in any way, are given below.

EXAMPLE 1

Preparation of a polysiloxane corresponding to the following formula:

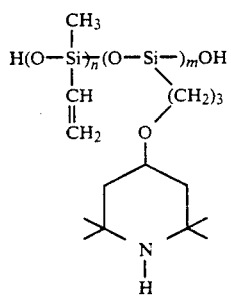

50 g of H₂O, 33.2 g (0.1 m) of methyldiethoxysilyl-3-oxypropyl-4-(2,2,6,6-tetramethyl) piperidine, 1.6 g (0.01 moles) of methyldiethoxyvinylsilane, 0.005 g of tin butyldilaurate are charged into a flask equipped with stirrer, condenser and thermometer.

The mixture is submitted to reflux heating until gas chromatography analysis shows that there are no longer any reagents present in the mixture.

80 cc of toluene are then added to the solution and the water layer is separated from the organic layer. The latter is washed with two 30 cc portions of water.

The organic layer is then evaporated, first at atmospheric pressure then under vacuum up to a temperature of 160° C. and at a pressure of 5 mm (Hg).

The product thus obtained is composed of a mixture of cyclic and linear products having an osmometric average molecular weight of 2700 Da and viscosity of approx. 30 Pa x sec at 20° C.

EXAMPLE 2

Preparation of the product corresponding to the following general formula.

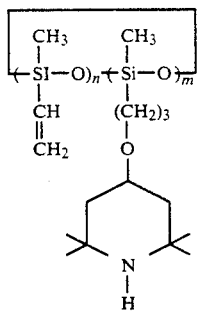

150 g of H₂O and 0.1 g of tin butyl dilaurate are added to 99.6 g (0.3 moles) of methyl diethoxysilyl-3-oxypropyl 4-(2,2,6,6-tetramethyl) piperidine and 16 g (0.1 moles) of methyldiethoxyvinylsilane.

The products are submitted to hydrolysis as described in Example 1. The water layer is then separated and the organic layer is heated to a temperature of approx. 80°-90° C. for 4 hours in the presence of 0.05 g of KOH. At the end of the reaction, the product is washed with water and the organic layer is evaporated as described in Example 1.

The viscous liquid residue has an average molecular weight of approx. 1000 Da and from HPLC analysis is shown to have a 90% content of cyclic products.

EXAMPLE 3

Preparation of the product corresponding to the following formula CH CH

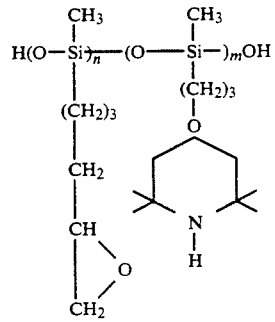

The same procedure is used as described in Example 1, substituting the diethoxymethylvinylsilane with diethoxymethyl, gammaglycidyloxypropylsilane.

EXAMPLE 4

Preparation of the product corresponding to the following general formula

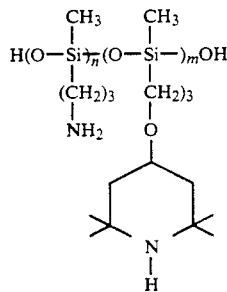

The same procedure is used as described in Example 1, substituting the diethoxymethylvinylsilane with gamma aminopropyldialkoxysilane in molar quantities of 1 for every 10 moles of methyldiethoxysilyl-3-oxypropyl piperidine.

EXAMPLE 5

Preparation of the product corresponding to the general formula

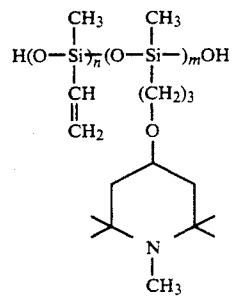

The same procedure is used as described in Example 1, substituting the diethoxymethyl 3 oxypropyl (4 (2,2,6,6)-tetramethyl piperidinyl)-silane with diethoxymethyl 3-oxypropyl-(4-(1,2,2,6,6-pentamethyl)-piperidinyl) silane, in the same molar ratio.

EXAMPLE 6

Preparation of the product corresponding to the general formula

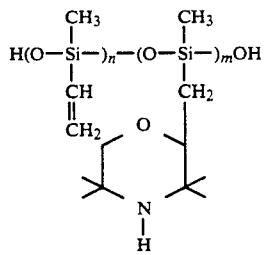

The same procedure is used as described in Example 1, substituting, in the same molar ratios, the diethyoxymethyl-3 oxypropyl (4(2,2,6,6 tetramethyl) piperidinyl) silane with diethoxymethyl methylene (2(3,3,5,5 tetramethyl) morpholinyl) silane.

EXAMPLE 7

Preparation of the product corresponding to the general formula

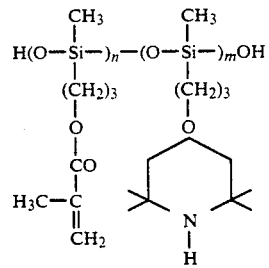

By substituting the diethoxymethylsilane with diethoxymethyl-methacryloxypropylsilane in the same molecular ratio as Example 1, a yellowish viscous liquid product is obtained, with an average osmometric molecular weight of 1900 Da.

EXAMPLE 8

Preparation of the compound corresponding to the general formula

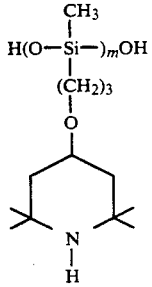

31.2 g (0.1 moles) of dichloromethyl 3 oxypropyl 4 (2,2,6,6tetramethyl)-piperidinyl) silane are added to 40 g of a 20% water solution of NaOH kept at a temperature of 40°–60° C.

At the end of the hydrolysis, toluene is added and the mixture is left at a temperature of 60° C. for a further 3 hours.

The organic layer is then separated from the water layer, washed twice with water and evaporated up to a temperature of 160° C. and 5mm Hg.

The product thus obtained is a mixture of cyclic and linear products (50/50) with an average viscosimetric molecular weight of 2500 Da.

EXAMPLE 9

Preparation of LDPE film. Each of the stabilizing compounds prepared as described in Examples 1, 2, 5, 6, 7, 8 has been mixed with commercial LDPE type Riblene A42CL using 10 parts by weight of the stabilizing compound for every 100 parts of the previously pulverized polymer.

The mixing process is carried out by heating the components at 90° C. for 1 hour in a powder mixer.

The masters thus obtained are diluted with another polymer to obtain mixtures containing 0.1 and 0.25% parts by weight of stabilizing compound for every 100 g of polymer.

In the same way a second series of mixtures have been prepared, further containing 0.01 g of diterbutylperoxide for every 100 parts of polymer.

All the mixtures thus obtained are passed through a Brabender laboratory draw-plate under the following conditions:

T: 125, 150, 175, 195, 190° C.

Number of screw revs: 20 rpm.

The compounds extruded in the above way are cut into chips and extruded again using the same draw-plate equipped with a flat head to obtain a 150 um thick film.

These films are exposed to UV rays using an ATLAS CI65 WOM device under the following operating conditions:

Temperature of the black panel: 60° C.

Relative humidity: 50%. Cycle in the presence of total light. Tensile tests are carried out at different exposure times to determine the elongation to break.

The table below shows the exposure time in WOM as number of hours necessary to decrease the elongation to break by 50% (t 50% AR).

TABLE 1

|  |  | t 50% AR (h) | t 50% AR with diterbutyl-peroxide[h] |
|---|---|---|---|
| Riblene A42CL |  | 100 | 90 |
| A42CL + 0,1% | prod. 8 | 1000 | 980 |
| A42CL + 0,25% | prod. 8 | 1300 | 1400 |
| A42CL + 0,1% | prod. 1 | 950 | 1600 |
| A42CL + 0,25% | prod. 1 | 1350 | 1900 |
| A42CL + 0,1% | prod. 2 | 1100 | 1700 |
| A42CL + 0,25% | prod. 2 | 1250 | 2100 |
| A42CL + 0,1% | prod. 7 | 1000 | 1800 |
| A42CL + 0,25% | prod. 7 | 1650 | 2000 |
| A42CL + 0,1% | prod. 5 | 750 | 1080 |
| A42CL + 0,25% | prod. 5 | 850 | 1200 |
| A42CL + 0,1% | prod. 6 | 1150 | 1750 |
| A42CL + 0,25% | prod. 6 | 1600 | 2400 |

EXAMPLE 10

Preparation of LDPE injection moulded specimen.

The same procedure is used for the preparation of the specimen as in the previous Example: LDPE masters (Riblene A42CL) are produced containing 10 parts by weight of products 1, 2, 5, 6, 8 for every 100 parts of polymer. These masters are then diluted until the concentration of the above products corresponds to 0.1% and 0.25% of the weight of the polymer.

At the same time, compounds of the same polymer are prepared, containing the same additives and diterbutylperoxide in a quantity of 0.01 parts by weight for every 100 parts of polymer.

All the mixtures thus obtained are passed through a Brabender draw-plate to obtain chips which are extruded in an injection moulding press until specimen having a thickness of approx. 1 mm are obtained.

These specimen are exposed to accelerated UV aging in the device specified.

At different exposure times of the specimen, tensile bars are obtained by punching, to determine their breaking load.

Table II below shows the exposure time in WOM necessary to obtain a 50% decrease of the initial breaking load (t 50%CR).

TABLE 2

| | | t 50% CR (h) | t 50% CR with diterbutylperoxide (h) |
|---|---|---|---|
| Riblene A 42CL | | 1000 | 1350 |
| A42CL + 0.1% | prod 8 | 5500 | 5400 |
| A42CL + 0,25% | prod 8 | 7300 | 6900 |
| A42CL + 0.1% | prod 1 | 5000 | 9000 |
| A42CL + 0,25% | prod 1 | 7100 | 12100 |
| A42CL + 0.1% | prod 2 | 5350 | 8300 |
| A42CL + 0,25% | prod 2 | 6959 | 10500 |
| A42CL + 0,1% | prod 5 | 4800 | 6000 |
| A42CL + 0.1% | prod 6 | 6300 | 8700 |

EXAMPLE 11

UV stabilization of an Acrylonitrile Butadiene Styrene resin.

A commercial ABS resin of the type Ravikral to which Alkanox 240 has been added in quantities of 0.2% of the weight of the resin, is mixed with the products of Examples 1, 2, 5, 7, 8 in quantities of 0.25 and 0.5 parts for 100 parts of resin.

The powder thus obtained is mixed for 10' in a Banbury mixer at a temperature of 190° C. and then extruded to obtain chips which are then moulded in a press under the following operating conditions:

| Preheating: | 3' |
|---|---|
| Moulding: | 3' |
| Temperature: | 170° C. |

3 mm thick specimen are obtained and exposed in WOM under the same conditions described in Example 9.

Table 3 below shows the results in terms of yellow index variation (ΔYI) with respect to the manufacture not exposed in WOM.

TABLE 3

| | YI after 500$_h$ in WOM | YI after 1000$_h$ in WOM |
|---|---|---|
| Ravikral | 12,52 | |
| Ravikral + 0.25% prod 8 | 6,25 | 15,50 |
| Ravikral + 0.5% prod 8 | 4,3 | 12,20 |
| Ravikral + 0.25% prod 1 | 3,2 | 6,55 |
| Ravikral + 0.5% prod 1 | 1,5 | 3,68 |
| Ravikral + 0.25% prod 2 | 2,82 | 5,95 |
| Ravikral + 0.5% prod 2 | 1,98 | 4,2 |
| Ravikral + 0.25% prod 5 | 1,05 | 3,3 |
| Ravikral + 0.25% prod 7 | 1,8 | 5,5 |

EXAMPLE 12

Preparation of polyamide films.

Commercial polyamide of the type Calaton CA of ICI in powder form is mixed with approx. 1% of each of the products obtained in Examples 1, 3, 4, 8.

After mixing, part of this powder is compression moulded to obtain film having a thickness of 50 um.

The compression moulding is carried out under the following conditions:

T: 180° C.
P: 200 Kg/cm$^2$
Moulding time: 3'.

The films are then submitted to accelerated UV aging in WOM used as described in the previous examples, and the yellow indexes are determined at different exposure times.

Table 4 shows the results obtained.

TABLE 4

| Yellow Index Variation (ΔYI) as a function of the exposure time in WOM (h). | | | | |
|---|---|---|---|---|
| | 250 (h) | 500 (h) | 1000 (h) | 1500(h) |
| Calaton CA | 3 | 10 | | |
| Calton CA + product 1 | 0,1 | 2 | 6 | 10 |
| Calaton CA + product 4 | 0,17 | 0,5 | 1,2 | 5 |
| Calaton CA + product 3 | 0,15 | 0,7 | 1,5 | 8 |
| Calaton CA + product 8 | 0,16 | 1,8 | 4,2 | 7.8 |

We claim:

1. A polymeric stabilizer of the formula (I),

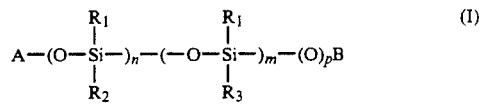

wherein, m and n, either the same or different, are integers between 1 and 50,

A and B, either the same or different, are —H, —Si(CH$_3$)$_3$, a linear or branched chain C$_1$-C$_6$ alkyl radical, or, A and B jointly represent a direct bond allowing for a cyclic structure, p is 0 when A and B are a direct bond and is 1 when A and B are not a direct bond, R$_1$ is methyl, phenyl, alkoxy, —OH, —OSi(CH$_3$)$_3$ or —OSi(OR)$_3$ radical, wherein R is a linear or branched alkyl radical, R$_2$ is one of the radicals:

13

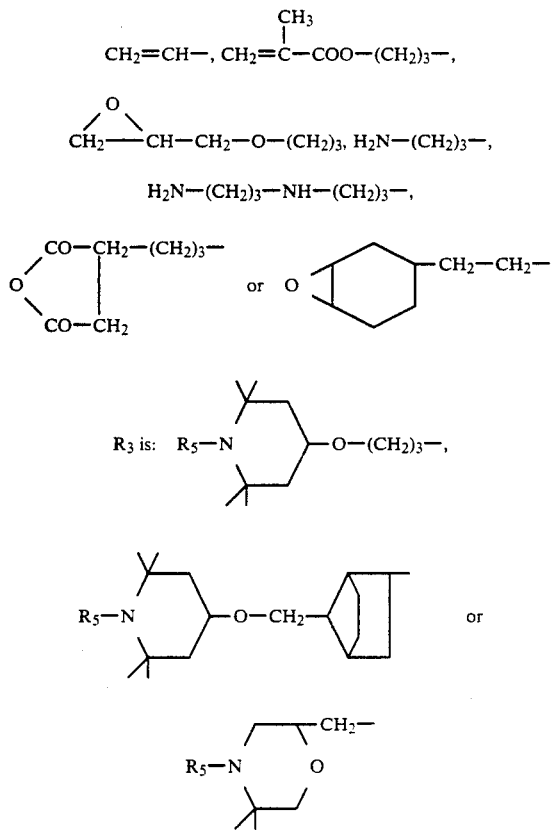

where $R_5$ is —H, —$CH_3$ or $C_6H_5$—$CH_2$—.

2. A polymeric stabilizer according to claim 1 having a random distribution of monomeric units and a linear or cyclic structure.

3. A polymeric stabilizer according to claim 1 where A and B jointly represent a direct bond wherein n and m are integers so that (n+m) is a number between 3 and 7.

4. A polymeric stabilizer according to claim 1, where A and B, either the same or different, are H, —Si($CH_3$)$_3$ or a linear or branched $C_1$-$C_6$ alkyl radical,
$R_1$=$CH_3$, and
$R_3$ is a group corresponding to the formula

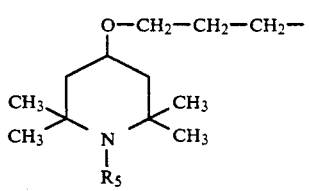

where $R_5$ has the meaning as defined in claim 1.

5. A process for the preparation of a stabilizer corresponding to the formula of structure (Ia):

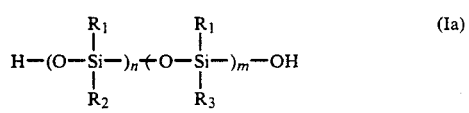

where $R_1$, $R_2$ and $R_3$ have the following meaning:

14

$R_1$ is a methyl, phenyl, alkoxy, —OH, —OSi($CH_3$)$_3$ or —OSi(OR)$_3$ radical, wherein R is a linear or branched alkyl radical,
$R_2$ is one of the radicals:

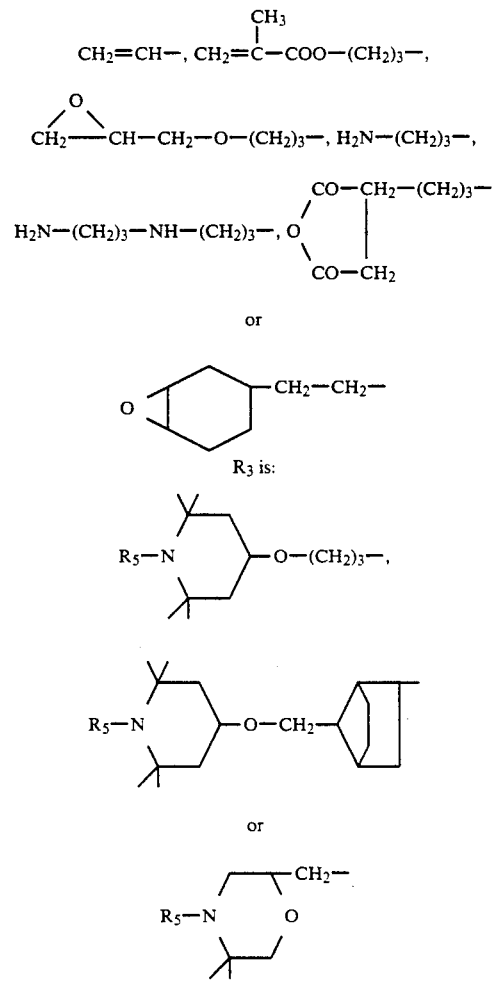

where $R_5$ is —H, —$CH_3$ or $C_6H_5$—$CH_2$—, comprising mixing and reacting in the presence of water
a) a dialkoxysilane corresponding to the general formula (II)

where, $R_1$ and $R_2$ have the meaning as defined above, and $R_6$ is a methyl or ethyl group, and
b) a dialkoxysilane corresponding to the general formula (III)

where $R_1$ and $R_3$ have the meaning as defined above, and $R_6$ is a methyl or ethyl group,
wherein the reaction is carried out at the reflux temperature with contact of alkoxysilanes a) and b)

being maintained for a period ranging from 2 to 10 hours, in the presence of tin dibutyllaurate, zinc octoate, tin actoate, or alkaline hydroxides as a reaction catalyst.

6. A process for the preparation of a stabilizer corresponding to the formula of structure (Ib)

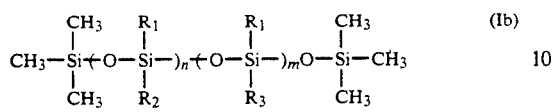

comprising mixing and reacting the polymer corresponding to the formula of structure (Ia)

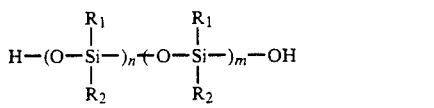

with trimethylchlorosilane, hexamethyldisiloxane or hexamethyldisilazane, wherein $R_1$ is a methyl, phenyl, alkoxy, —OH, —OSi(CH$_3$)$_3$ or —OSi(OR)$_3$ radical, wherein R is a linear or branched alkyl radical, $R_2$ is one of the radicals:

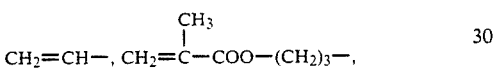

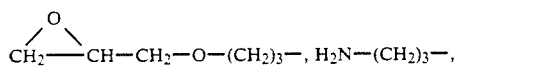

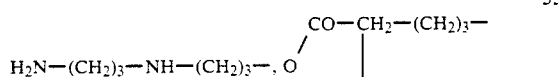

or

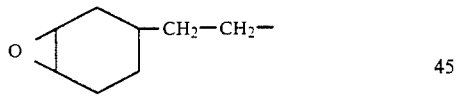

$R_3$ is:

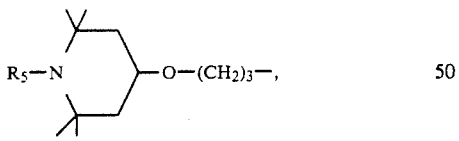

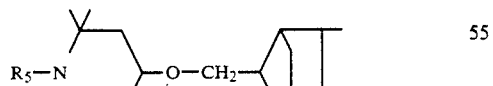

or

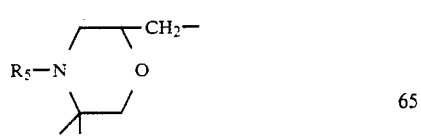

where $R_5$ is —H, —CH$_3$ or C$_6$H$_5$—CH$_2$—, and wherein the reaction is carried out at a temperature ranging from 20° to 120° C. over a period ranging from 1 to 5 hours.

7. A process for the preparation of a stabilizer corresponding to the formula of structure

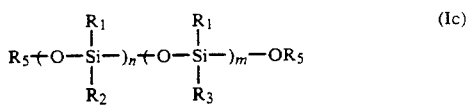

wherein $R_1$, $R_2$ and $R_3$ have the following meaning:

$R_1$ is a methyl, phenyl, alkoxy, —OH,—OSi(CH$_3$)$_3$ or —OSi(OR)$_3$ radical, wherein R is a linear or branched alkyl radical, $R_2$ is one of the radicals:

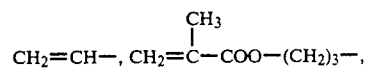

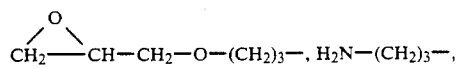

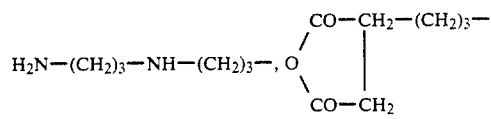

or

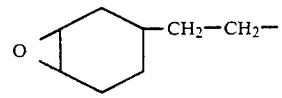

$R_3$ is:

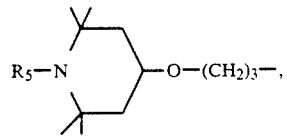

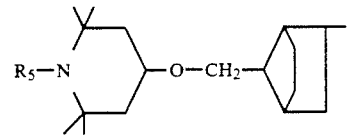

or

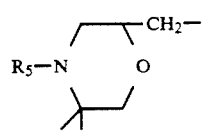

and $R_5$ is a linear or branched chain $C_1$-$C_6$ alkyl radical, comprising reacting a polymer corresponding to formula (Ia)

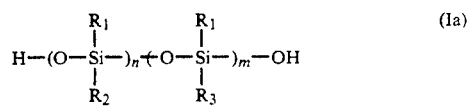

wherein $R_1$, $R_2$ and $R_3$ are as above defined, with a compound of the formula $R_5$OH, wherein $R_5$ is as above defined, wherein the reaction is carried out at a temperature ranging from 80° to 130° C. over a period ranging from 1 to 8 hours in the presence of KOH, zinc oxide, tin dibutyldilaurate, tin butyltrilaurate, tin tributyllaruate or alkali metal alcoholates.

8. A composition comprising an organic polymer and an effective stabilizing amount of a polymeric stabilizer as defined by claim 1, wherein the organic polymer is a polyolefin, copolymer of an olefin with acrylic acid or maleic anhydride, polyester, polyamide, or polyurethane.

9. A composition according to claim 8, wherein the organic polymer is EPDM or a polycarbonate.

10. A composition comprising an organic polymer and an effective stabilizing amount of a polymeric stabilizer as defined by claim 1, wherein the organic polymer is a synthetic rubber.

* * * * *